(12) United States Patent  
Hanebuchi

(10) Patent No.: US 7,281,798 B2  
(45) Date of Patent: Oct. 16, 2007

(54) OPTOMETRY APPARATUS

(75) Inventor: Masaaki Hanebuchi, Kota-cho (JP)

(73) Assignee: Nidek Co., Ltd., Gamagori (JP)

( * ) Notice: Subject to any disclaimer, the term of this patent is extended or adjusted under 35 U.S.C. 154(b) by 32 days.

(21) Appl. No.: 11/389,241

(22) Filed: Mar. 27, 2006

(65) Prior Publication Data

US 2006/0221301 A1 Oct. 5, 2006

(30) Foreign Application Priority Data

Mar. 31, 2005 (JP) ............................. 2005-104608

(51) Int. Cl.  
*A61B 3/10* (2006.01)
(52) U.S. Cl. ...................... 351/205; 351/206; 351/211
(58) Field of Classification Search ................ 351/205, 351/206, 209, 211, 216  
See application file for complete search history.

(56) References Cited

U.S. PATENT DOCUMENTS

| 3,880,502 | A | * | 4/1975 | Humphrey | ................. 351/246 |
| 4,679,921 | A | | 7/1987 | Yamada et al. | |
| 5,309,186 | A | * | 5/1994 | Mizuno | ....................... 351/212 |
| 5,483,305 | A | | 1/1996 | Kohayakawa et al. | |

2002/0047993 A1 4/2002 Takeuchi et al.

FOREIGN PATENT DOCUMENTS

| JP | A-1-129830 | 5/1989 |
| JP | A 02-213320 | 8/1990 |
| JP | A-11-70076 | 3/1999 |

* cited by examiner

*Primary Examiner*—Huy Mai  
(74) *Attorney, Agent, or Firm*—Oliff & Berridge, PLC

(57) ABSTRACT

An optometry apparatus comprising: a target projecting optical system adapted for diopter movement, for projecting a target onto a fundus of an examinee's eye to form an image of the target on the fundus, wherein the target projecting optical system including: an objective lens to be positioned at the front of the examinee's eye: a relay lens arranged so that a front focal point of the relay lens coincides with an approximate conjugate point of an anterior segment of the examinee's eye with respect to the objective lens positioned at the front of the examinee's eye; a plus-power lens arranged at the approximate conjugate point of the anterior segment with respect to the positioned objective lens, the plus-power lens having refractive power determined so that a front focal point of the plus-power lens coincides with an approximate conjugate point of the fundus with respect to the positioned objective lens; and an astigmatism correction optical element arranged between the relay lens and the plus-power lens, for correcting astigmatism of the examinee's eye.

5 Claims, 2 Drawing Sheets

OPTOMETRY APPARATUS

BACKGROUND OF THE INVENTION

1. Field of the Invention

The present invention relates to an optometry apparatus for examining or measuring an examinee's eye.

2. Description of Related Art

As a target projecting optical system of an optometry apparatus such as an eye refractive power measurement apparatus, an optometer, and an eye accommodation measurement apparatus, an optical system having diopter movement means and astigmatism correction means has been known (e.g., Jpn. unexamined patent publication No. 11-70076(1999)). The diopter movement means is adapted to perform diopter movement by for example moving a target in a direction of a projection optical axis of the target projecting optical system or moving a lens in the direction of the projection optical axis. For a downsized apparatus, it is preferred that a moving amount (range) of the diopter movement means such as the target and the lens is as small as possible. On the other hand, the astigmatism correction means is adapted to perform astigmatism correction by for example rotating two cross-cylinder lenses about the projection optical axis respectively. To clearly present the target to the examinee's eye, it is preferred that the target is less affected by aberration of the astigmatism correction means such as the cross-cylinder lenses.

BRIEF SUMMARY OF THE INVENTION

The present invention has an object to provide an optometry apparatus adapted to reduce a moving amount (range) of diopter movement means and to prevent a target from becoming affected by aberration of astigmatism correction means to clearly present the target to an examinee's eye.

Additional objects and advantages of the invention will be set forth in part in the description which follows and in part will be obvious from the description, or may be learned by practice of the invention. The objects and advantages of the invention may be realized and attained by means of the instrumentalities and combinations particularly pointed out in the appended claims.

To achieve the purpose of the invention, there is provided an optometry apparatus comprising: a target projecting optical system adapted for diopter movement, for projecting a target onto a fundus of an examinee's eye to form an image of the target on the fundus, wherein the target projecting optical system including: an objective lens to be positioned at the front of the examinee's eye; a relay lens arranged so that a front focal point of the relay lens coincides with an approximate conjugate point of an anterior segment of the examinee's eye with respect to the objective lens positioned at the front of the examinee's eye; a plus-power lens arranged at the approximate conjugate point of the anterior segment with respect to the positioned objective lens, the plus-power lens having refractive power determined so that a front focal point of the plus-power lens coincides with an approximate conjugate point of the fundus with respect to the positioned objective lens; and an astigmatism correction optical element arranged between the relay lens and the plus-power lens, for correcting astigmatism of the examinee's eye.

BRIEF DESCRIPTION OF THE DRAWINGS

The accompanying drawings, which are incorporated in and constitute a part of this specification illustrate an embodiment of the invention and, together with the description, serve to explain the objects, advantages and principles of the invention.

In the drawings.

DETAILED DESCRIPTION OF THE PREFERRED EMBODIMENTS

Figure 1:
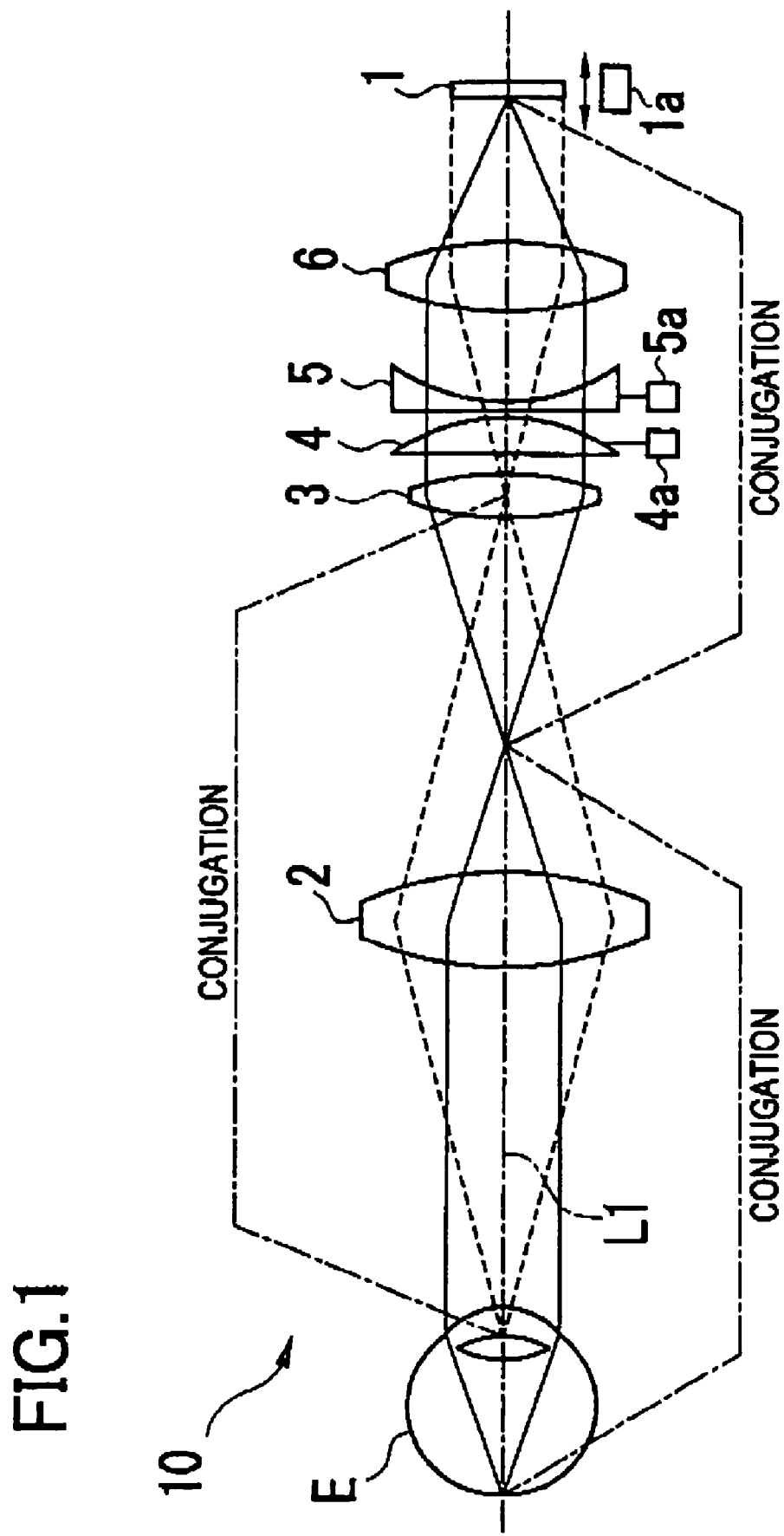
FIG. 1 is a schematic configuration view of a target projecting optical system in a first embodiment.

A detailed description of preferred embodiments of the present invention will now be given referring to the accompanying drawings. FIG. 1 is a schematic configuration view of a target projecting optical system of an optometry apparatus in a first embodiment of the present invention. This target projecting optical system 10 is configured to project a target 1 onto a fundus of an examinee's eye E through an optical system (optical elements) mentioned later and form an image of the target 1 on the fundus. The target 1 is accordingly presented to the examinee's eye E. The target 1 is illuminated by an illumination light source not shown and is arranged to be movable in a direction of a projection optical axis L1 of the target projecting optical system 10 by means of a movement mechanism 1a in order to adjust diopter of the examinee's eye E (diopter movement). Furthermore, the target projecting optical system 10 includes an objective lens 2 to be positioned at the front of the examinee's eye E, a pupil conjugate lens 3 arranged at an approximate conjugate point of a pupil of the eye E with respect to the objective lens 2 positioned at the front of the eye E, two cross-cylinder lenses 4 and 5 serving as astigmatism correction optical elements for correcting astigmatism of the eye E if necessary, and a relay lens 6 arranged so that a front focal point thereof coincides with the approximate conjugate point of the pupil E with respect to the objective lens 2 positioned at the front of the eye E.

The pupil conjugate lens 3 arranged at the approximate conjugate point of the pupil is a plus-power lens having refractive power determined so that a front focal point thereof coincides with an approximate conjugate point of the fundus with respect to the objective lens 2 positioned at the front of the eye E. Accordingly, when the target 1 is moved to the approximate conjugate point of the fundus, target luminous flux from the target 1 passes, in the form of substantially parallel luminous flux, through the two cross-cylinder lenses 4 and 5. At this time, the pupil conjugate lens 3, arranged at the approximate conjugate point of the pupil, has little influence on changes in magnification of the target image formed on the fundus.

In the present embodiment, as an example, the refractive power of the pupil conjugate lens 3 is determined so that the front focal point thereof coincides with the approximate conjugate point of the fundus of the eye E that is emmetropia (normal). The reason why the emmetropic eye is regarded as a reference as above is in that, when the target 1 is moved to the approximate conjugate point of the fundus of a hyperopic or myopic eye, the target luminous flux which passes through the cross-cylinder lenses 4 and 5 may be convergent or divergent luminous flux; however, the inclination of such convergent or divergent luminous flux is so gentle or slight with respect to the projection optical axis L1 as to restrain the occurrence of aberration. This is because the convergent or divergent luminous flux which are symmetric with respect to (the case of) the emmetropic eye will pass through the cross-cylinder lenses 4 and 5.

When the target 1 is moved along the projection optical axis L1 by the movement mechanism 1a, a presenting position (a presenting distance) of the target 1 to the eye E is optically changed, thereby performing diopter movement. The target 1 can be moved as above to the approximate conjugate point of the fundus regardless of refractive error of the eye E. The target 1 shall be moved toward the eye E if it is myopia (shortsighted), whereas the target 1 shall be moved away from the eye E if it is hyperopia (farsighted).

The cross-cylinder lens 4 is rotated about the projection optical axis L1 by a rotation mechanism 4a and the cross-cylinder lens 6 is rotated about the same axis L1 by a rotation mechanism 5a respectively to correct an astigmatic component of the eye E. The two cross-cylinder lenses 4 and 5 are for example cylindrical lenses having refractive powers equal in absolute values. The combination of the lenses 4 and 5 may be any one of the following combinations; a combination of a cylindrical concave lens and a cylindrical convex lens as shown in FIG. 1, a combination of cylindrical convex lenses, a combination of a cylindrical convex lens and a cylindrical concave lens, and a combination of cylindrical concave lenses.

Operations of the target projecting optical system 10 having the above structure will be described below. In the following example, the examinee's eye E is emmetropia and the pupil conjugate lens 3 used here has the refractive power determined so that the front focal point of the lens 3 coincides with the approximate conjugate point of the fundus of the emmetropic eye.

The target luminous flux from the target 1 moved to the approximate conjugate point of the fundus is collimated into substantial parallel luminous flux by the relay lens 6, then passes through the two cross-cylinder lenses 5 and 4, and is focused on the approximate conjugate point of the fundus by the pupil conjugate lens 3. This focused luminous flux is collimated again into substantial parallel luminous flux by the objective lens 2 and then is focused onto the fundus, forming the target image thereon.

Since the target luminous flux from the target 1 passes, in the form of substantial parallel luminous flux, through the two cross-cylinder lenses 4 and 5 as above, restraining the occurrence of aberration, the target image can be formed well on the fundus. Consequently, the high-resolution and clear target 1 be presented to the examinee's eye E. Since the relay lens 6 is arranged so that the front focal point thereof coincides with the approximate conjugate point of the pupil, furthermore, the apparent size of the target 1 remains unchanged even when the presenting position of the target 1 is optically changed. The approximate conjugate point of the pupil is formed between the target 1 and the examinee's eye E, so that the presenting position of the target 1 can optically be changed by movement of the target 1 in a reduced moving amount (moving range).

In the present embodiment, the pupil conjugate lens 3 is designed to have the refractive power determined with reference to the emmetropic eye, but it is not limited thereto. Preferably, an eye having refractive power in a range of −6D to +6D is regarded as the reference in order to present a high-resolution and clear target 1 to an eye which is frequently measured.

In the present embodiment, the plus-power lens (the pupil conjugate lens 3 in the present embodiment) having the refractive power determined so that its front focal point coincides with the approximate conjugate point of the fundus with respect to the objective lens 2 arranged at the front of the examinee's eye E is arranged at the approximate conjugate point of the pupil with respect to the objective lens 2 positioned at the front of the eye E. Alternatively, the plus-power lens may be arranged at an approximate conjugate point of an anterior segment of the examinee's eye E such as an approximate conjugate point of a cornea of the eye E with respect to the objective lens 2 positioned at the front of the eye E. Further, the relay lens 6 in the present embodiment is arranged so that its front focal point coincides with the approximate conjugate point of the pupil with respect to the objective lens 2 positioned at the front of the examinee's eye E. Alternatively, the relay lens 6 may be arranged so that its front focal point coincides with the approximate conjugate point of the anterior segment such as the approximate conjugate point of the cornea with respect to the objective lens 2 positioned at the front of the eye E.

The two cross-cylinder lenses 4 and 5 arranged between the pupil conjugate lens 3 and the relay lens 6 are preferably arranged near the pupil conjugate lens 3. In such arrangement, the positions of the two cross-cylinder lenses 4 and 5 are close to the approximate conjugate point of the pupil. It is therefore possible to remedy a problem that the target 1 is viewed as a distorted shape.

Figure 2:
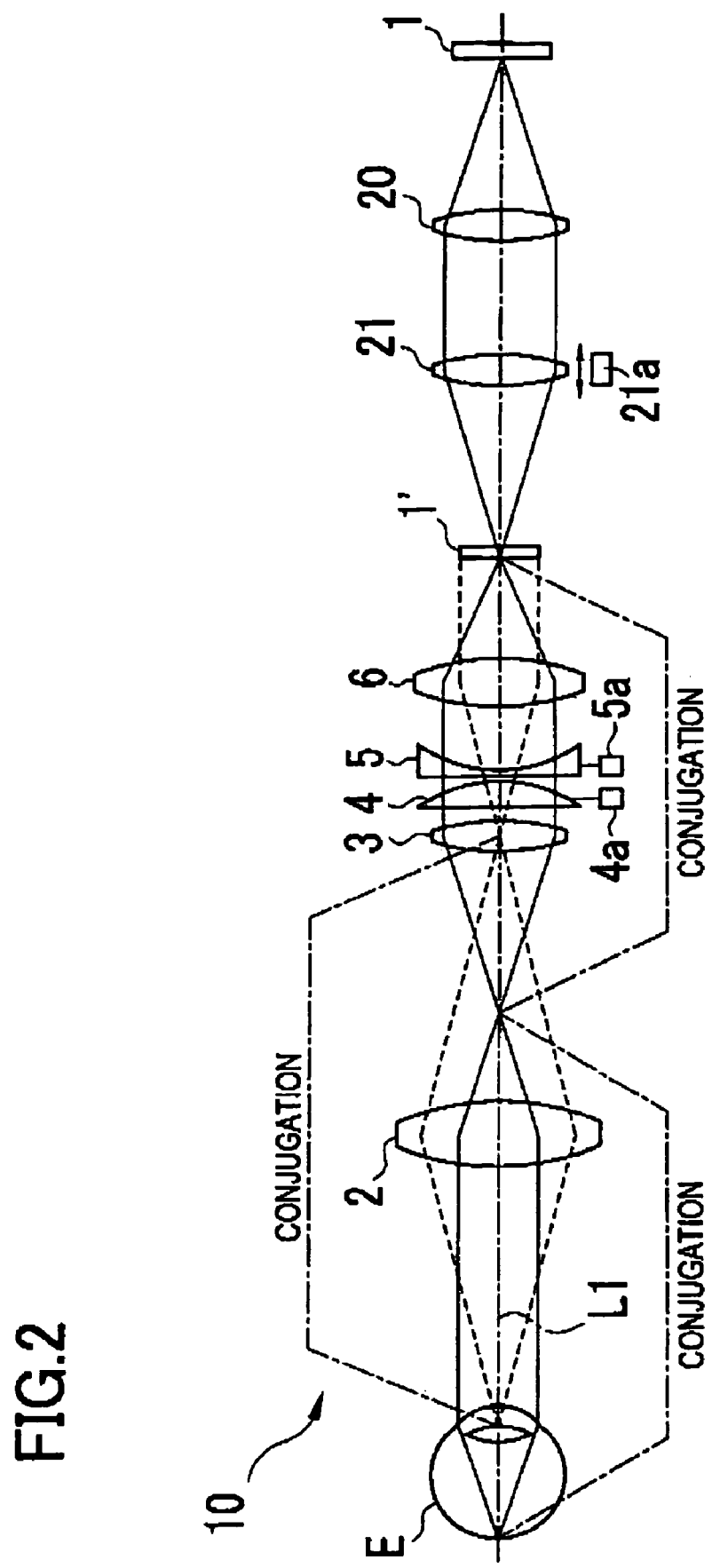
FIG. 2 is a schematic configuration view of a target projecting optical system in a second embodiment.

FIG. 2 is a schematic configuration of a target projecting optical system of an optometry apparatus in a second embodiment of the present invention. This target projecting optical system 10 is configured to form a target image 1' by means of a collimator lens 20 arranged so that the target 1 is arranged at a back focal point of the lens 20 and a lens 21 arranged to be movable in the direction of the projection optical axis L1 by a movement mechanism 21a. In this case, the presenting position (presenting distance) of the target 1 is optically changed by movement of the lens 21. With the above structure, the presenting position of the target 1 can optically be changed even by movement of the lens 21 in a reduced moving amount (moving range).

It is noted that the optometry apparatus having the target projecting optical system 10 in the present embodiment may includes an eye refractive power measurement apparatus, an eye accommodation measurement apparatus, and others. In the eye refractive power measurement apparatus, for example, the target projecting optical system 10 operates to adjust (diopter movement) or correct (astigmatism correction) myopia, hyperopia, or astigmatism of an examinee's eye based on spherical power, astigmatic power (cylindrical power), and an angle of a cylindrical axis of the examinee's eye obtained by a well known eye refractive power measurement optical system. Consequently, an examinee is allowed to compare differences in visibility of the target 1 before and after the adjustment (diopter movement) or the correction (astigmatism correction). In the eye accommodation measurement apparatus, for example, the target 1 is moved toward an examinee's eye after correction of the astigmatism of the eyes so that the accommodation function of the eye is obtained out of consideration of the astigmatism of the eye.

While the presently preferred embodiment of the present invention has been shown and described, it is to be understood that this disclosure is for the purpose of illustration and that various changes and modifications may be made without departing from the scope of the invention as set forth in the appended claims.

What is claimed is:

1. An optometry apparatus comprising:

a target projecting optical system adapted for diopter movement, for projecting a target onto a fundus of an examinee's eye to form an image of the target on the fundus, wherein the target projecting optical system including:

an objective lens to be positioned at the front of the examinee's eye;

a relay lens arranged so that a front focal point of the relay lens coincides with an approximate conjugate point of an anterior segment of the examinee's eye with respect to the objective lens positioned at the front of the examinee's eye;

a plus-power lens arranged at the approximate conjugate point of the anterior segment with respect to the positioned objective lens, the plus-power lens having refractive power determined so that a front focal point of the plus-power lens coincides with an approximate conjugate point of the fundus with respect to the positioned objective lens; and an astigmatism correction optical element arranged between the relay lens and the plus-power lens, for correcting astigmatism of the examinee's eye.

2. The optometry apparatus according to claim 1, wherein the astigmatism correction optical element is two cross-cylinder lenses arranged at a position near to the plus-power lens between the relay lens and the plus-power lens, the cross-cylinder lenses being rotatable about an optical axis of the target projecting optical system respectively.

3. The optometry apparatus according to claim 1, wherein the target projecting optical system includes diopter movement means for optically changing a presenting position of the target.

4. The optometry apparatus according to claim 1, wherein the target is arranged to be movable in a direction of an optical axis of the target projecting optical system.

5. The optometry apparatus according to claim 1, wherein the target projecting optical system includes a lens arranged between the target and the relay lens to be movable in a direction of an optical axis of the target projecting optical system.

* * * * *